(12) United States Patent
Villwock et al.

(10) Patent No.: US 12,070,319 B2
(45) Date of Patent: Aug. 27, 2024

(54) OLFACTORY DIAGNOSTIC AND TRAINING KITS AND METHODS

(71) Applicant: University of Kansas, Lawrence, KS (US)

(72) Inventors: Jennifer Villwock, Shawnee, KS (US); Kevin Sykes, Shawnee, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 371 days.

(21) Appl. No.: 17/281,121

(22) PCT Filed: Oct. 1, 2019

(86) PCT No.: PCT/US2019/054000
§ 371 (c)(1),
(2) Date: Mar. 29, 2021

(87) PCT Pub. No.: WO2020/072448
PCT Pub. Date: Apr. 9, 2020

(65) Prior Publication Data
US 2021/0353206 A1 Nov. 18, 2021

Related U.S. Application Data

(60) Provisional application No. 62/878,486, filed on Jul. 25, 2019, provisional application No. 62/735,585, filed on Oct. 1, 2018.

(51) Int. Cl.
*A61B 5/00* (2006.01)

(52) U.S. Cl.
CPC ..... *A61B 5/4011* (2013.01); *A61B 2560/0487* (2013.01)

(58) Field of Classification Search
CPC .......... A61B 5/4011; A61B 2560/0487; A61B 5/381; G01N 33/0001
See application file for complete search history.

(56) References Cited

U.S. PATENT DOCUMENTS

| 2015/0177202 A1 | 6/2015 | Ozbek et al. |
| 2017/0227548 A1 | 8/2017 | Henkin |
| 2020/0253531 A1* | 8/2020 | Smith .................. A61B 5/4088 |

FOREIGN PATENT DOCUMENTS

WO      2014113645 A1      7/2014

OTHER PUBLICATIONS

Jiang, R.-S., & Liang, K.-L. (2015). A pilot study of the self-administered computerized olfactory testing system. American Journal of Rhinology & Allergy, 29(2). https://doi.org/10.2500/ajra.2015.29.4177 (Year: 2015).*

(Continued)

*Primary Examiner* — Matthew Kremer
*Assistant Examiner* — Elina Sohyun Ahn
(74) *Attorney, Agent, or Firm* — STINSON LLP

(57) ABSTRACT

Disclosed herein are olfactory diagnostic kits and methods for screening for an olfactory dysfunction. Also disclosed are olfactory training kits and methods for treating an olfactory dysfunction in a subject. Also disclosed is a method for diagnosing a subject for an olfactory dysfunction. Also disclosed is a method for training a subject with an olfactory dysfunction.

5 Claims, 5 Drawing Sheets

(56) References Cited

OTHER PUBLICATIONS

Niklassen, A. S., Ovesen, T., Fernandes, H., Fjaeldstad, A. W. (2017). Danish validation of Sniffin' sticks olfactory test for threshold, discrimination, and identification. The Laryngoscope, 128(8), 1759-1766. https://doi.org/10.1002/lary.27052 (Year: 2017).*

Burghart extended smelltest 2-phenylethanol. Sense Trading—Smell Test. (2017, June 1). Retrieved Apr. 3, 2023, from https://web.archive.org/web/20170601173825/http://smelltest.eu/en/product/extended-complete-test-sniffin-sticks-2-phenylethanol (Year: 2017).*

Burghart Smell Quartet smelltraining. Sense Trading—Smell Test. (2017, Dec. 19). Retrieved Apr. 3, 2023, from https://web.archive.org/web/20171219231728/https://www.smelltest.eu/en/product/burghart-smell-quartet-smelltraining-sniffin-sticks/ (Year : 2017).*

Streicher, C. (2015, Mar. 31). Aromatherapy tips: Improve your sense of smell. Amrita Aromatherapy. https://www.amrita.net/blog/aromatherapy-tips-improve-your-sense-of-smell/, hereto referred as Streicher. (Year: 2015).*

Visser, M. (2013, July). Blending essential oils for beginners. Growing Up Herbal. https://growingupherbal.com/blending-essential-oils-for-beginners/, hereto referred as Visser. (Year: 2013).*

Plant Therapy Diffusible 10 mL Essential Oil Blends, Top 6 Organic (3 Pack). Walmart. (2017, Jul. 14). https://www.walmart.com/ip/Plant-Therapy-Diffusible-10-mL-Essential-Oil-Blends-Top-6-Organic-3-Pack/501828243, hereto referred as Plant Therapy, and in view of Natural Perfumery. (Year: 2017).*

Natural Perfumery Beginner's kit. Perfumers Apprentice—Natural Perfumery Beginner's Kit. (2017, August 5). https://web.archive.org/web/20170805071340/https://shop.perfumersapprentice.com/p-6633-natural-perfumery-beginners-kit.aspx, hereto referred as Natural Perfumery. (Year: 2017).*

International Search Report issued for PCT/US2019/054000, mailed Dec. 4, 2019.

* cited by examiner

OLFACTORY DIAGNOSTIC AND TRAINING KITS AND METHODS

CROSS-REFERENCE TO RELATED APPLICATIONS

This application is a National Stage of International Application No. PCT/US2019/054000, filed Oct. 1, 2019, which claims benefit of U.S. Provisional Application No. 62/739,585, filed Oct. 1, 2018, and Application Ser. No. 62/878,486, filed Jul. 25, 2019, which are hereby incorporated herein by reference in their entireties.

BACKGROUND

Smell identification and discrimination directly reflect not only the health of the sinonasal cavity, but also the cognitive state and higher cortical centers as the olfactory nerve is a direct connection to the brain (Stockhorst U, et al. Physiol Behay. 2004 83(1):3-11; Bastir M, et al. Nature Communications. 2011 2:588; Sigurdardottir S, et al. Neuropsychology. 2016 30(1):98-108). This is because olfaction is the oldest and most primal sense. It has not only been preserved, but refined and enhanced, throughout the millennia (Sarafoleanu C, et al. J Med Life. 2009 2(2):196-198). Olfaction has an impact on multiple facets of daily living such as the enjoyment of food, nutritional status, and ability to detect spoilage; detection of safety hazards such as fire or natural gas; livelihood; socialization; and overall quality of life (Stockhorst U, et al. Physiol Behay. 2004 83(1):3-11; Sarafoleanu C, et al. J Med Life. 2009 2(2):196-198).

Olfactory dysfunction (OD) is very well described in the neurocognitive disorder literature. For example, every study published investigating Alzheimer's disease (AD) directly links OD and AD (Doty R L. Neurobiol Dis. 2012 46(3): 527-552). An alternate diagnosis should be strongly considered if a patient suspected of having AD does not have OD (Hummel T, et al. GMS Curr Top Otorhinolaryngol Head Neck Surg. 2012 10; Sun G H, et al. Laryngoscope. 2012 122(7):1455-1462). This is because abnormal amyloid and tau protein deposits occur in the olfactory bulb and tract early in the disease course of AD. In fact, they often precede any symptoms of cognitive decline (Bahar-Fuchs A, et al. Journal of Alzheimer's Disease. 2010 22(4):1081-1087; Devanand D P, et al. Neurology. 2015 84(2):182-189). One current area of research in AD is focused on screening tools to identify patients at risk for this condition as well as those who exhibit abnormal brain protein deposits on amyloid-position emission tomography (PET) but are cognitively normal. Interestingly, these PET scans are often indistinguishable from patients with AD (Villemagne V L, et al. Nat Rev Neurol. February 2018; Villemagne V L, et al. J Alzheimers Dis. 2013 33 Suppl 1:S349-359). Comparing such PET-positive, disease negative individuals with PET-positive, disease positive individuals may lead to breakthroughs in the understanding of the pathophysiologic mechanisms of AD and how to more effectively combat it.

Unsurprisingly, there is also a link between OD and brain injury. While not necessarily sensitive, OD following head trauma is specific for concomitant abnormalities and evidence of trauma on imaging studies (Charland-Verville V, et al. Am J Rhinol Allergy. 2012 26(3):222-226; Bakker K, et al. Brain Inj. 2016 30(2):191-198; Proskynitopoulos P J, et al. Surg Neurol Int. 2016 7(Suppl 10):S263-S275; Xydakis M S, et al. Neurology. 2015 84(15):1559-1567; Schofield P W, et al. Front Neurol. 2014 5). Additionally, it was recently illustrated that amyloid deposits occur in the brains of pediatric and young-adult athletes who experienced repetitive, sub-concussive injuries (Gavett B E, et al. Clin Sports Med. 2011 30(1):179-xi). This may explain the 100% specificity noted in prior studies of OD for intracranial radiographic abnormalities (Proskynitopoulos P J, et al. Surg Neurol Int. 2016 7(Suppl 10):5263-5275; Gavett B E, et al. Clin Sports Med. 2011 30(1):179-xi). This has important implications for "return-toplay" guidelines in sports where head trauma is common as well as in the military. OD testing could be easily and rapidly utilized to help clarify the extent of brain injury. For example, based on the research mentioned above, should an athlete or solider experience a decrement in olfactory function following injury, the trauma was likely significant enough to cause brain injury, and they should be referred for further evaluation and placed on protective activity restrictions.

It is similarly well established that OD occurs in a variety of disease states that impact the health of the sinonasal cavity. These include, at a minimum, chronic sinusitis (CRS), allergic rhinitis (AR), nasal polyposis (NP), and post-traumatic OD thought to be due to shearing trauma of the olfactory nerve. Prevalence of OD ranges from 30-85% in these conditions (Banglawala S M, et al. Int Forum Allergy Rhinol. 2014 4(12):986-994; Kohli P, et al. Am J Rhinol Allergy. 2016 30(6):402-406; Haxel B R, et al. Laryngoscope Investig Otolaryngol. 2017 2(5):269-275; DeConde A S, et al. Int Forum Allergy Rhinol. 2014 4(9):725-733). Medical and surgical therapies aim to correct anatomic or functional derangements and restore optimal function. In patients with these chronic conditions, recurrence is possible even with appropriate management (Bakhshaee M, et al. Iran J Otorhinolaryngol. 2016 28(85): 125-134). In such cases, if the recurrence is detected after it has progressed beyond mild mucosal inflammation, it can be difficult to treat without revision surgery. For this reason, early detection of recurrence is key and a cost-effective, reusable, user-friendly test of OD would allow for patient self-monitoring of olfactory function. Should decrements be noted prior to scheduled follow-up, the patient could call to be seen sooner and potentially have interventions initiated that obviate the need for revision surgery, resulting in reduced related morbidity and costs.

A modality for at-home olfactory monitoring is needed as, should unexpected OD be noted, follow-up is warranted for initiation of more aggressive medical management to potentially obviate the need for revision sinus surgery. Similarly, using OD to screen patients with suspected dementia would allow for more accurate diagnoses—the absence of OD precludes a diagnosis of AD—and the ability to monitor disease progression or treatment response (Pelton G H, et al. Alzheimer Dis Assoc Disord. 2016 30(1):67-69; Tabert M H, et al. Ann Neurol. 2005 58(1):155-160; Growdon M E, et al. Neurology. 2015 84(21):2153-2160).

In short, increased accessibility of smell tests would provide valuable information regarding patient clinical course, and, ultimately, enable cost-effective enhanced individualized care and optimization of the diagnostic and therapeutic plans for patients with sinonasal and neurocognitive issues.

Unfortunately, the most commonly used commercially available test—the University of Pennsylvania Smell Identification Test (UPSIT)—costs approximately $25 for a single use, scratch and sniff booklet that expires within six months of receipt. This financial burden makes olfactory testing inaccessible. It almost certainly precludes regular outpatient olfactory monitoring for disease progression or treatment response.

SUMMARY

Disclosed herein is an olfactory diagnostic kit for screening for an olfactory dysfunction comprising a panel of from 4 to 20 diagnostic fragrances. One of the goals of this technology is the utilization of commercially available essential oils to maximize ease of use, availability, and adaptability to cultural differences in familiar scents. The ideal test uses the minimum number of scents needed to achieve sufficient sensitivity and specificity. Based on pilot data, a panel of no fewer than 4, but no more than 20 is expected to be adequate. This may vary depending on specific pathology (for example, Alzheimer's disease versus sinonasal disease versus concussion/head trauma) and culture in which the test is deployed. For example, more aromatic spice scents may be more appropriate for the population in India.

The kit comprises a plurality of aroma inhalers, each dosed with an essential oil fragrance from the panel of diagnostic fragrances, and an answer key. In some embodiments, the answer key first prompts a user to use an inhaler and confirm whether an aroma could be detected, wherein if the answer is yes, then the answer key prompts for identification of the aroma among a list of choices, wherein if the answer is no, the user can try another inhaler with a higher dose of the essential oil fragrance until either the user reaches a maximum dose or is able to answer in the affirmative. By first asking the user to confirm whether they can smell the aroma, the kit can distinguish between misidentification and lack of detection. Therefore, in some embodiments, the kit comprises aroma inhalers with a series of doses for each fragrance, such as double strength, quadruple strength, and octuple strength. In some embodiments if the user is unable to detect odorant at the octuple strength concentration, they will be coded as completely anosmic. In some embodiments, if the user indicates that they do detect the odorant, but are unable to correctly identify it at least twice, then dosage can be increased until they are able to correctly identify it. In some embodiments, sinonasal pathology is thought to cause an overall decrease in smell on the nose side. Pathologies like Alzheimers disease, which impact the brain and higher cortical functions, are thought to have more difficulty identifying the odors. Pathologies like Alzheimer's disease are thought to have difficulty both detecting and identifying the odors. The difficulty with identification reflects the impact of Alzheimer's disease on the brain and higher cortical functions.

The answer key can take any suitable form, depending on the environment. In some cases, the answer key is a computer interface. In some cases, the answer key is a document, chart, card, or book. In some cases, the answer key is designed to be filled out by a medical professional recording the user's answers. In other cases, the answer key is designed to be followed and filled out by the user. In these embodiments, the answer key can include an additional prompt to make sure the user selects the correct inhaler.

Also disclosed is a method for diagnosing a subject for an olfactory dysfunction, that involves providing a panel of from 4 to 20 diagnostic fragrances, prompting the subject to use an aroma inhaler dosed with an essential oil fragrance from the panel of diagnostic fragrances; prompting the subject to confirm whether an aroma could be detected, wherein if the answer is yes, further prompting the subject to identify the aroma from among a list of choices, wherein if the answer is no, repeating these steps with a higher dose of the essential oil fragrance until the subject answers yes or reaches a maximum dose; repeating these steps with new aroma inhalers containing the same essential oil fragrance until the subject answers correctly at least two times in a row, or reaches a maximum number of incorrect answers; and repeating these steps with each essential oil fragrance in the panel of diagnostic fragrances.

Also disclosed is an olfactory training kit for treating an olfactory dysfunction in a subject comprising a panel of from 4 to 20 training fragrances. In some embodiments, the use of more scents provides a more robust response to the training. In some embodiments, the training kit will be customized based on the subject's olfactory dysfunction with the inclusion of scents they have difficulty detecting and identifying. However, as olfactory training requires the participant to intentionally smell each scent at least twice a day, an excessive number of fragrances can be time prohibitive. The kit comprises a plurality of aroma inhalers, each dosed with an essential oil fragrance from the panel of training fragrances and an instruction key. In some embodiments, the panel of training fragrances does not consist of rose, eucalyptus, lemon, and/or cloves. In some embodiments, the panel of training fragrances does not comprise rose, eucalyptus, lemon, and/or cloves. In some embodiments, the instruction key identifies the fragrance in each aroma inhaler and prompts the subject to use each aroma inhaler for at least 5 seconds, including about 5 to 10 seconds. They can then take a brief pause of 5 to 10 seconds and intentionally sniff that same inhaler again. After another pause, they then move on to the next scent.

In some embodiments, the essential oil fragrance dose is personalized based on the subject's baseline olfaction. This can be determined empirically by a medical professional and used to design the training schedule. In some cases, the kit contains a plurality of aroma inhalers for each essential oil fragrance at different dosages so the medical professional can prescribe a dose that fits their olfaction needs. In other embodiments, the kit can be personalized by the medical professional to contain each essential oil fragrance at a pre-determined dosage.

Also disclosed is a method for training a subject with an olfactory dysfunction that involves providing a panel of from 4 to 20 training fragrances, prompting the subject to use an aroma inhaler dosed with an essential oil fragrance from the panel of fragrances while noting the identity of the fragrance for at least 5 seconds, and repeating this step with each essential oil fragrance in the panel of training fragrances. In some embodiments, the panel of training fragrances does not consist of rose, eucalyptus, lemon, and/or cloves.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
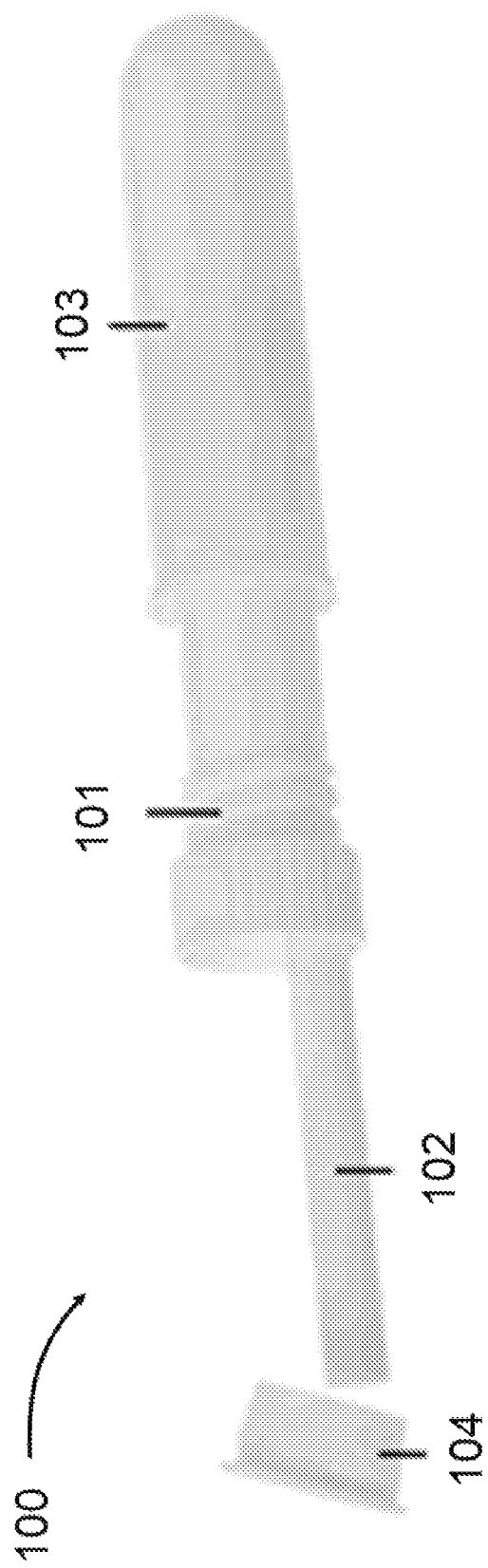
FIG. 1 is an embodiment of an aroma inhaler for use in the disclosed kits and methods. Briefly, the aroma inhaler includes an internal absorbent wick, to which the essential oil and odorless carrier oil can be applied. The wick is housed within a perforated inner housing that allows airflow around the wick that carries the scent to the nose of the person inhaling the aroma. A non-perforated outer housing is applied when the inhaler is not in use and provides an air tight seal to prevent dispersal and weakening of aromas and protect the inner components.

The disclosed kits and methods involve the use of aroma inhalers dosed with essential oil fragrances. Essential oils are volatile and liquid aroma compounds from natural sources, usually plants. They are not oils in a strict sense, but often share with oils a poor solubility in water. Essential oils often have an odor and are therefore used in food flavoring and perfumery. They are usually prepared by fragrance extraction techniques (such as distillation, cold pressing, or Solvent extraction). Essential oils are distinguished from aroma oils (essential oils and aroma compounds in an oily solvent), infusions in a vegetable oil, absolutes, and concretes. Typically, essential oils are highly complex mixtures of often hundreds of individual aroma compounds.

Examples of known essential oils include Agar oil, Ajwain oil, Angelica root oil, Anise oil, Asafoetida oil, Balsam of Peru, Basil oil, Bay oil, Bergamot oil, Birch oil, Black pepper oil, Buchu oil, Camphor oil, Cannabis flower essential oil, Calamodin oil, Caraway seed oil, Cardamom seed oil, Carrot seed oil, Cedar oil, Chamomile oil, Calamus oil, Cinnamon oil, Citron oil, Citronella oil, Clary Sage oil, Coconut oil, Clove oil, Coffee oil, Coriander oil, Costmary oil, Costus root oil, Cranberry seed oil, Cubeb oil, Cumin seed oil, Cypress oil, Cypriol oil, Curry leaf oil, Davana oil, Dill oil, Elecampane oil, Elemi oil, Eucalyptus oil, Fennel seed oil, Fenugreek oil, Fir oil, Frankincense oil, Galangal oil, Galbanum oil, Garlic oil, Geranium oil, Ginger oil, Goldenrod oil, Grapefruit oil, Henna oil, Helichrysum oil, Hickory nut oil, Horseradish oil, Hyssop, Idaho-grown Tansy, Jasmine oil, Juniper berry oil, Laurus nobilis, Lavender oil, Ledum, Lemon oil, Lemongrass, Lime, Litsea cubeba oil, Linalool, Mandarin, Marjoram, Melissa oil, Mentha arvensis oil, Moringa oil, Mountain Savory, Mugwort oil, Mustard oil, Myrrh oil, Myrtle, Neem oil, Nutmeg oil, Orange oil, Oregano oil, Orris oil, Palo Santo, Parsley oil, Patchouli oil, Perilla essential oil, Pennyroyal oil, Peppermint oil, Petitgrain, Pine oil, Ravensara, Red Cedar, Roman Chamomile, Rose oil, Rosehip oil, Rosemary oil, Rosewood oil, Sage oil, Sandalwood oil, Sassafras oil, Savory oil, Schisandra oil, Spearmint oil, Spikenard, Spruce oil, Star anise oil, Tangerine, Tarragon oil, Tea tree oil, Thyme oil, Tsuga, Turmeric, Valerian, Warionia, Vetiver oil, Western red cedar, Wintergreen, Yarrow oil, Ylang-ylang, and Zedoary.

Common aromatic qualities include floral, citrus, fruity, sweet, spicy, minty, and pungent. Olfactory dysfunction patterns are pathology-specific (Nordin S, et al. Acta Otolaryngol. 1998 118(2):226-34; Jimbo, et al. Psychogeriatrics. 2011 11(4):196-204). It is therefore important that the essential oils eligible for inclusion represent a wide array of distinct aromatic qualities.

Exposure to odors varies by culture and can impact performance on olfactory tests. For example, Chinese subjects perform 15% better on a culturally appropriate version of the UPSIT versus the standard version. Scents such as cinnamon were therefore excluded. (Feng G, et al Chem Senses. 2019 44(3):189-195). Despite geographic proximity, the suitability of the Chinese test in Taiwan has been questioned, underscoring the importance of a readily adaptable olfactory testing and training models. (Feng et al 2019). Similarly, a Scandanavian version can eliminate scents such as talc, black pepper, tea, lavender, gasoline, and coffee. (Nordin S, et al. Acta Otolaryngol. 1998 118(2):226-34).

As shown in FIG. 1, a typical aroma inhaler 100 comprises an absorbent material 102 and container 101, such as a cylinder, for containing the absorbent material 102 that contains perforations to allow inhalation of the aromas inside the container and a cap 104 for replacing the absorbent material 102. The absorbent material 102 can be dosed with a known amount of one or more essential oils and optionally a carrier oil (e.g. jojoba or grapeseed oil) and then inserted into the cylinder. The device also optionally includes a cover 103 to seal the aromas inside the device when not in use. Aromatherapy inhalers are commercially available and can be adapted for use in the disclosed devices, its, and methods.

The answer key can take any suitable form, depending on the environment. In some cases, the answer key is a computer interface. In some cases, the answer key is a document, chart, card, or book. In some cases, the answer key is designed to be filled out by a medical professional recording the user's answers. In other cases, the answer key is designed to be followed and filled out by the user. In these embodiments, the answer key can include an additional prompt to make sure the user selects the correct inhaler.

Figure 5:
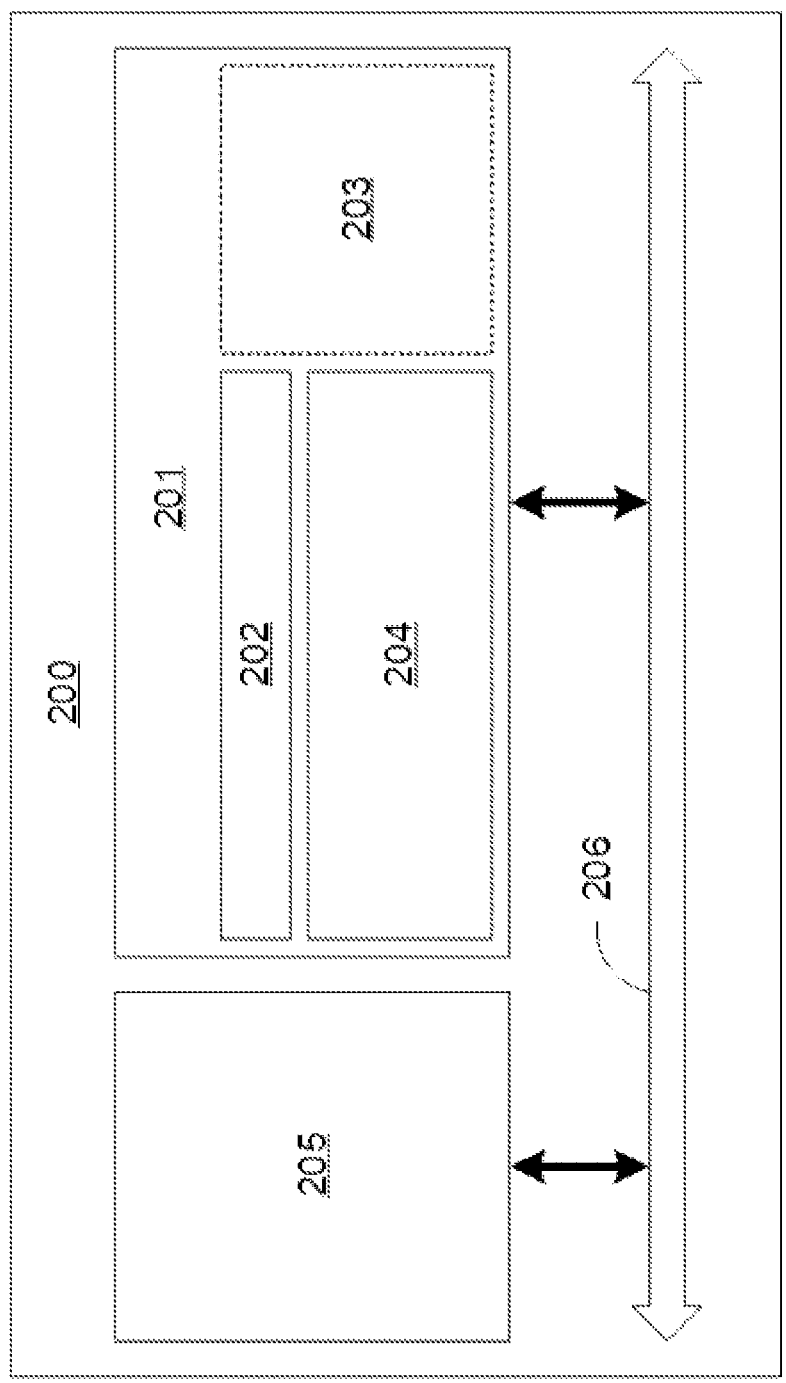
FIG. 5 illustrates an example of a computing device that can be used with the AROMA system in accordance with various embodiments of the present disclosure.

Referring now to FIG. 5, shown is an example of a computing device 200 that can be included with disclosed AROMA system. The computing device 200 can include at least one processor circuit, for example, having a processor 205 and a memory 201, both of which are coupled to a local interface 206. To this end, the computing device(s) 200 may comprise, for example, a computer, laptop, smartphone, tablet, or other mobile processing unit providing computing capability. The computing device(s) 200 may include, for example, one or more display devices such as cathode ray tubes (CRTs), liquid crystal display (LCD) screens, gas plasma-based flat panel displays, LCD projectors, or other types of display devices, etc. The computing device(s) 1103 may also include, for example various peripheral devices. In particular, the peripheral devices may include input devices such as, for example, a keyboard, keypad, touch pad, touch screen, microphone, scanner, mouse, joystick, or one or more push buttons, etc. Even though the computing device 200 is referred to in the singular, it is understood that a plurality of computing devices 200 may be employed in the various arrangements as described above. The local interface 206 may comprise, for example, a data bus with an accompanying address/control bus or other bus structure as can be appreciated.

Stored in the memory 201 are both data and several components that are executable by the processor 205. In particular, stored in the memory 201 and executable by the processor 205 are an answer key 206 and potentially other applications. Also stored in the memory 201 may be a data store 203 and other data. In addition, an operating system 202 may be stored in the memory 201 and executable by the processor 205. The data store 203 may be may be located in a single computing device or may be dispersed among many different devices.

It is understood that there may be other applications that are stored in the memory 201 and are executable by the processor 205 as can be appreciated. Where any component discussed herein is implemented in the form of software, any one of a number of programming languages may be employed such as, for example, C, C++, C#, Objective C, Java, Java Script, Perl, PHP, Visual Basic, Python, Ruby, Delphi, Flash, or other programming languages.

A number of software components are stored in the memory 201 and are executable by the processor 205. In this respect, the term "executable" means a program file that is in a form that can ultimately be run by the processor 205. Examples of executable programs may be, for example, a compiled program that can be translated into machine code in a format that can be loaded into a random access portion of the memory 201 and run by the processor 205, source code that may be expressed in proper format such as object code that is capable of being loaded into a random access portion of the memory 201 and executed by the processor 205, or source code that may be interpreted by another executable program to generate instructions in a random access portion of the memory 201 to be executed by the processor 205, etc. An executable program may be stored in any portion or component of the memory 201 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 201 is defined herein as including both volatile and nonvolatile memory and data storage components. Volatile components are those that do not retain data values upon loss of power. Nonvolatile components are those that retain data upon a loss of power. Thus, the memory 201 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 205 may represent multiple processors 205 and the memory 201 may represent multiple memories 201 that operate in parallel processing circuits, respectively. In such a case, the local interface 206 may be an appropriate network that facilitates communication between any two of the multiple processors 205, between any processor 205 and any of the memories 201, or between any two of the memories 201, etc. The local interface 206 may comprise additional systems designed to coordinate this communication, including, for example, performing load balancing. The processor 205 may be of electrical or of some other available construction.

Although the answer key, and other various systems described herein, may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application described herein, including an answer key that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Affordable Rapid Olfaction Measurement Array (AROMA): An Essential Oil-Based Test Strongly Correlated with UPSIT and Subjective Outcome Measures The goals of this study are to describe the development of the Affordable, Rapid, Olfactory Measurement Array (AROMA)—an essential oil-based test—and its test-retest reliability. AROMA was compare to the University of Pennsylvania Smell Identification Test (UPSIT) in healthy controls and those with sinonasal disease. Of note, the UPSIT was selected as a validated comparator as it is also a test intended for screening and at-home or in-clinic use. Secondary outcomes included correlation of AROMA and UPSIT with age and subjective sinonasal health outcomes.

Methods:

This project was reviewed by the University of Kansas Medical Center Institutional Review Board and approved prior to commencement of study activities; all participants signed an approved informed consent document.

Scents were chosen on their availability in essential oil format and high levels of familiarity and identifiability (Hummel T, et al. Chem Senses. 1997 22(1):39-52). Of note, multiple essential oils, when undiluted, had scents that were overpowering and prevented correct odor identification. For this reason, only dilutions were used in the development of the AROMA. Dilutions were based on pilot studies (unpublished data) in which five dilutions of each essential oil, diluted in an odorless diluent oil were prepared. The dilutions were presented, in random order, to fifteen normosmic subjects. Subjects were asked to indicate if an odor was present and, if so, to identify it. Based on these results, two dilutions for each essential oil were included in AROMA. The first, and lower, dilution was able to be correctly detected and identified by at least 80% of normal subjects. The second, and higher, dilution was twice this concentration.

Per manufacturer instructions (Aura Cacia, Norway, IA), the essential oils selected were all stable at room temperature for at least 18 months. Out of an abundance of caution, each AROMA was replaced every three months.

AROMA includes 14 essential oil scents at two concentrations. To complete the AROMA, participants are presented with an inhalant stick in random order and asked to determine if a scent is present or not. No blindfolding is required as all inhalant sticks are identical. Additionally, the inhalant sticks are only labeled by numbers. The scoring key was not made available to subjects. If the subject detects a scent, they complete a three-alternative (four response options), forced-choice response. The proportion of detected, and correctly identified, smells is calculated. It has taken approximately 10 minutes for subjects with normal cognition to complete AROMA. It is important to note that AROMA is intended to be a self-administered, point of care test. Its simple design—open inhaler stick, inhale, choose from multiple choice options if scent is detected—allows for self-administration. However, to ensure uniformity in olfactory testing for this study, AROMA was administered in a proctored setting.

Participants without sinonasal disease were prospectively recruited to assess the reliability of AROMA utilizing a test-retest protocol. The AROMA test was repeated a minimum of 48 hours after the initial test, but less than 1 week, to minimize likelihood of significant change in sinonasal health.

Further evaluation of AROMA was performed and compared with UPSIT utilizing a cohort of participants with diagnosed sinonasal disease (chronic sinusitis without polyposis and allergic rhinitis patients presenting to the Rhinology clinic—Sinonasal Cohort) and without (Healthy Cohort). Participants completed the SNOT-22, UPSIT and AROMA during the same visit. Each individual was additionally asked to rate their perceived loss of smell on a six-point ordinal scale (1—no problem; 2—very mild problem; 3—mild problem; 4—moderate problem; 5—severe problem; 6—problem as bad as it can be). In an attempt to avoid olfactory fatigue, a minimum of five minutes was allowed between olfactory tests. The UPSIT was completed per manufacturer instructions.

Exclusion criteria included: documented anosmia secondary to known surgical removal, or agenesis, of olfactory apparatus; history of never being able to detect smell; suspected malingering; neurocognitive or psychiatric disorders; and age <18 years or >90 years.

Study data were collected and managed using REDCap electronic data capture tools hosted at the University of Kansas Medical Center (Harris P A, et al. J Biomed Inform. 2009 42(2):377-381). Data were analyzed with SPSS version 24 (Armonk, NY). Group comparisons were performed using Mann-Whitney and Chi-Squared tests, as appropriate. Descriptive statistics on the percentage of correct answers for AROMA and UPSIT were reported using mean and 95% Wald confidence intervals. The test-retest reliability coefficient for AROMA was assessed in the healthy cohort using Pearson's correlation coefficient between the initial and follow-up AROMA scores. In the sinonasal cohort, Spearman's rho was used to determine the degree of correlation between each smell score (initial AROMA and UPSIT) and an individual's rated sense of smell. Spearman's rho was additionally used to determine the relationship between AROMA (initial visit) and UPSIT for the combined cohort; and their correlations with SNOT-22, patient age, and perceived sense of smell were recorded. Spearman's rho correlation coefficients were compared between groups using the Fisher r-to-z transformation. The Wilcoxon signed rank test was used to compare AROMA scores for high versus low concentrations.

Results:

Test-Retest of AROMA 37 healthy participants completed the test-retest protocol for AROMA as outlined in the methods. The cohort was 57% female and had a mean age of 45 years (95% CI: 39-50 years). The percent correct remained relatively stable between visits (75% [95% CI: 70%-80%] vs 78% [95% CI: 73%-84%]); with a test-retest reliability coefficient of 0.846 ($p<0.001$).

Population Completing AROMA Vs UPSIT Comparison 68 participants (n=30 Healthy Cohort, n=38 Sinonasal Cohort) completed both the AROMA and UPSIT evaluations. The gender distribution in the healthy cohort did not statistically differ from the sinonasal cohort (53% female vs. 68% female, respectively; p=0.204). As expected, the two groups differed based on UPSIT olfactory diagnostic categories and SNOT-22 scores (Table 1).

TABLE 1

Participant Characteristics

|  | Healthy Cohort (n = 30) | Sinonasal Cohort (n = 38) | Total |
|---|---|---|---|
| Age, y; mean (95% CI) | | | |
|  | 41 (36-46) | 55 (50-60) | 49 (45-53) |
| Gender; n (%) | | | |
| Female | 16 (53.3%) | 26 (68.4%) | 26 (38.2%) |
| Male | 14 (46.7%) | 12 (31.6%) | 42 (61.8%) |
| SNOT-22; mean (95% CI) | | | |
|  | 7.3 (4.2-10.4) | 50.6 (42.9-58.4) | 31.5 (24.7- |
| UPSIT Category Compressed; n (%) | | | |
| Normosmia | 22 (73.3%) | 10 (26.3%) | 32 (47.1%) |
| Hyposmia* | 8 (26.7%) | 28 (73.7%) | 36 (52.9%) |

*Hyposmia = Mild Microsmia, Moderate Microsmia, Severe Microsmia, or Anosmia

AROMA Evaluation of Sinonasal Cohort

Figure 2:
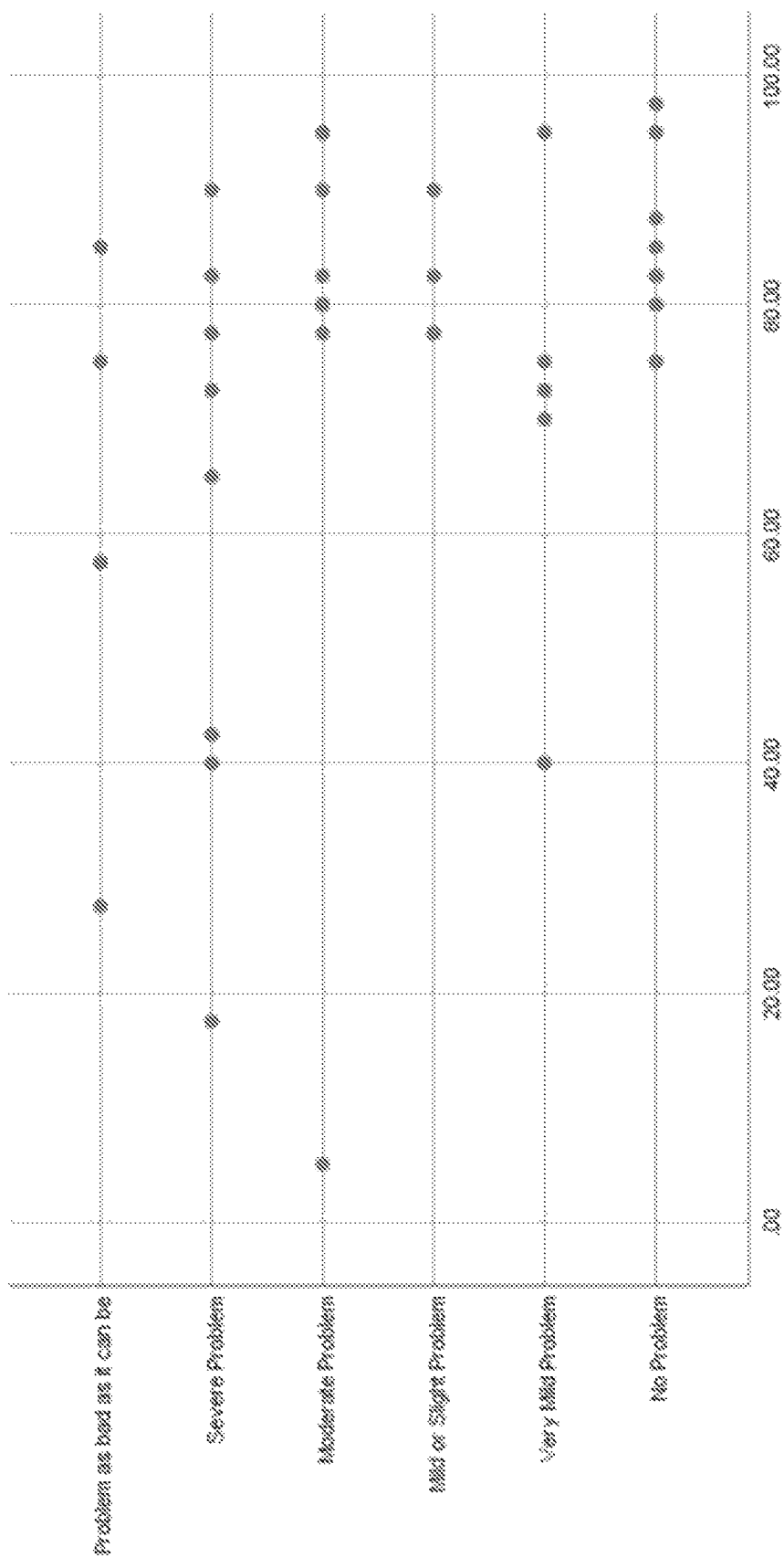
FIG. 2 is a plot of perceived smell loss versus AROMA percentage correct for the sinonasal cohort.

The sinonasal cohort scored worse than the healthy cohort, achieving a mean of 47% correct (95% CI: 40%-53%). An individual's perceived loss of smell was recorded on a six-point ordinal scale (1, no problem-6, problem as bad as it can be) and a scatterplot against the AROMA score was created (FIG. 2). Spearman's rho between the two variables was found to be −0.514 (p=0.001) and demonstrated agreement between subjective smell loss and AROMA score.

High Versus Low Concentration Results of AROMA

Figure 3:
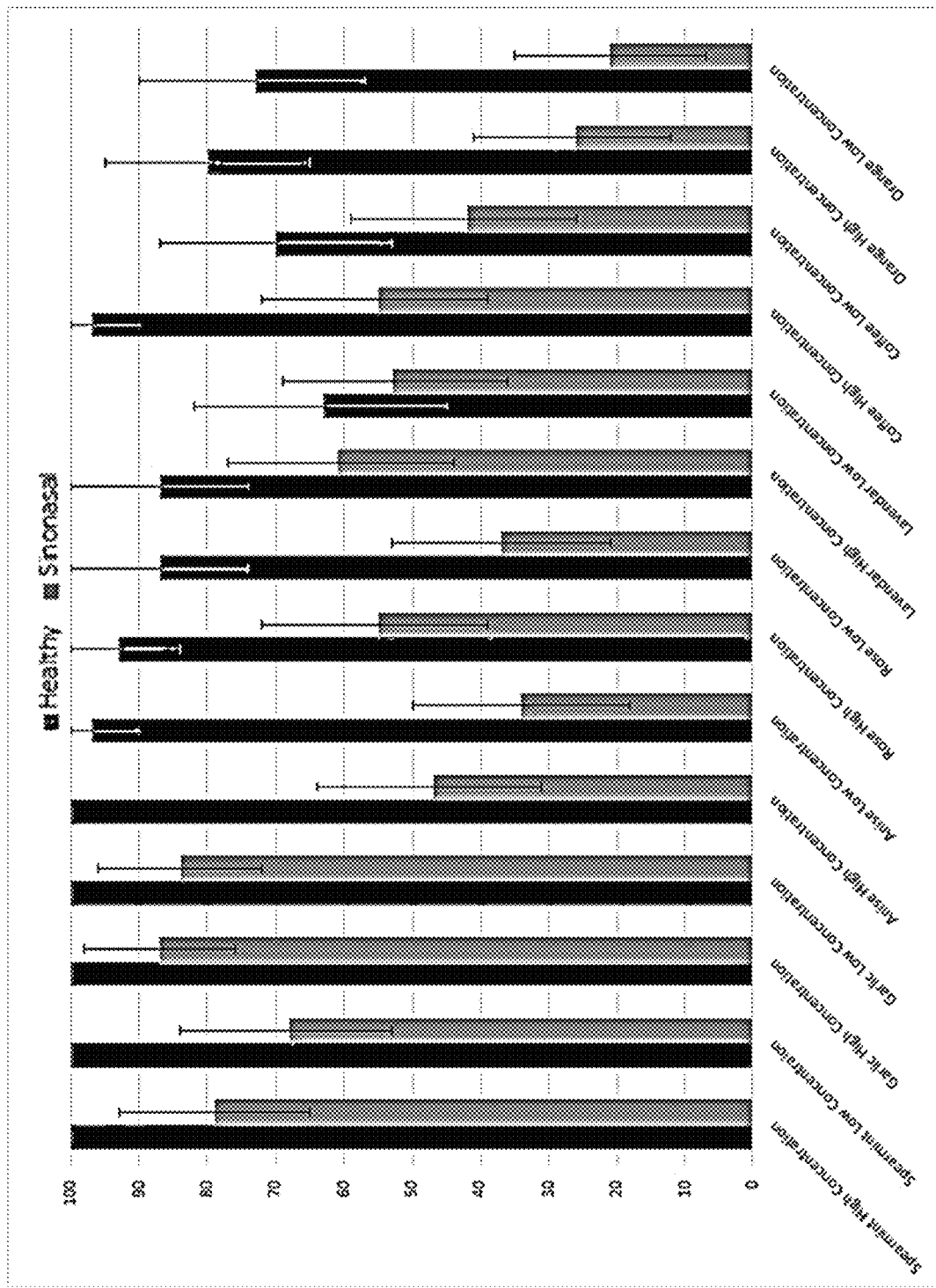
FIG. 3 shows mean percentage correct for AROMA scents of interest along with 95% confidence intervals.

The healthy population scores were 10% greater when utilizing a high-concentration scent (82% [95% CI: 77%-87%] vs 72% [95% CI: 66%-77%], p<0.001). This magnitude of difference was closely mirrored in the sinonasal cohort (49% [95% CI: 41%-57%] vs 41% [95% CI: 33%-49%], p=0.001). Interestingly, the discernment of scent at a low concentration was affected by the scent; certain scents were particularly difficult to identify in the sinonasal cohort regardless of concentration (FIG. 3). For example, high concentration orange was correctly identified by only 26% of the sinonasal cohort. The largest magnitude of difference in percentage of correct scent identification between the healthy and sinonasal cohorts was 63% and occurred with low concentration anise (97% vs 34%, respectively).

UPSIT Results and Comparison with AROMA

Figure 4:
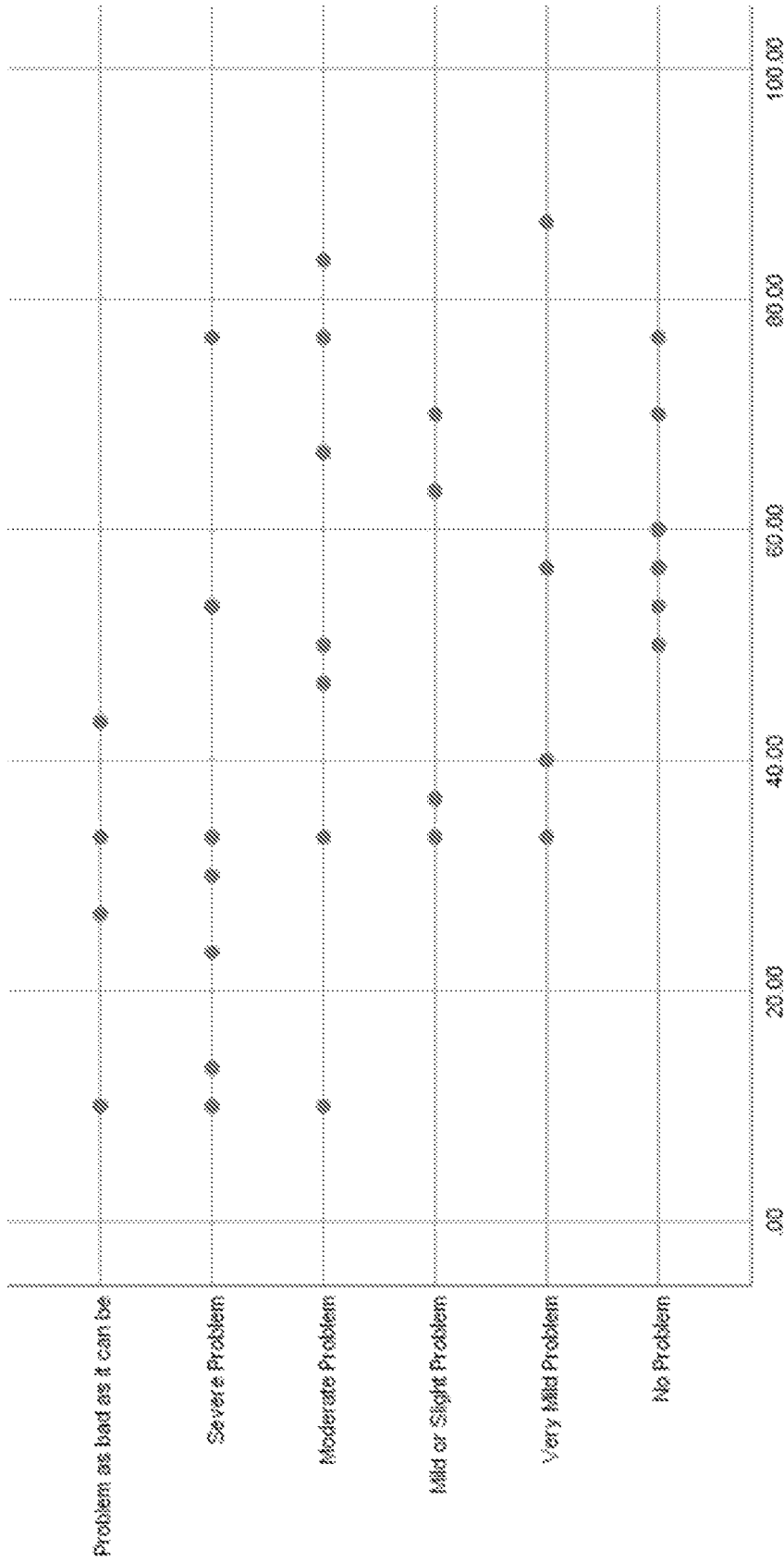
FIG. 4 is a plot of perceived smell loss versus UPSIT percentage correct for the sinonasal cohort.

The healthy population scored 88% correct (95% CI: 85%-92%) on UPSIT; while the sinonasal cohort scored 73% correct (95% CI: 65%-80%). The degree of perceived loss of smell in the sinonasal cohort was plotted against the UPSIT score (FIG. 4). Spearman's rho between the two variables was found to be −0.405 (p=0.012) and comparison with Spearman's rho from AROMA (p=−0.514, FIG. 2) was insignificant (p=0.562). To further evaluate correlations between AROMA and UPSIT, the cohorts were combined. Spearman's rho correlation of AROMA to UPSIT was statistically significant at p=0.749 (p<0.001). SNOT-22, age, and perceived sense of smell were all significantly correlated with both AROMA and UPSIT (Table 2). While the magnitude of correlation was greater for AROMA than UPSIT, pairwise comparison of the correlation coefficients was insignificant with respect to SNOT-22, age, and perceived sense of smell (p=0.190, p=0.453, p=0.424, respectively). Analysis of the cohorts separately was also done. In the healthy group, Spearman's rho correlation of AROMA to UPSIT was moderate at 0.488 (p=0.006); in the sinonasal group, the correlation was strong at p=0.790 (p<0.001).

SNOT-22, age, and perceived sense of smell were all statistically significantly correlated with both AROMA. Correlation of subjective metrics was stronger for AROMA than the UPSIT.

These results indicate increase sensitivity of AROMA for OD. Subjects universally scored higher on the UPSIT than AROMA. The increased magnitude of correlation between AROMA and age, perceived loss of smell, and SNOT-22 compared with the UPSIT all indicate increased sensitivity for OD of AROMA. Overall AROMA correlation to UPSIT is strong at r=0.75; lack of a stronger correlation, especially in the healthy cohort, may reflect the increased difficulty, and sensitivity, of AROMA for subtle OD. This is supported by the finding that AROMA better categorizes the subjective degree of smell loss. For example, subjects indicating moderate or worse loss of sense of smell still scored greater than 80% correct on the UPSIT.

Interestingly, ease of smell detection and identification was impacted by odorant. This is consistent with prior studies in Alzheimer's Disease and Parksinson's Disease showing that decrements in identification of particular scents are specific for these pathologies (Chou K L, et al. Parkinsonism Relat Disord. 2009 15(9):640-643; Woodward M R, et al. Am J Geriatr Psychiatry. 2018 26(8):835-846). For example, in the sinonasal cohort, orange was only identified correctly by 26% of subjects. Rose and anise were also problematic for the sinonasal cohort. In contrast, spearmint, garlic, anise, and coffee were consistently correctly identified by the healthy cohort. This may indicate that pathology-specific odorants may increase the utility of olfactory testing for the purposes of disease screening, monitoring, and evaluation of response to interventions. However, the average age of this cohort was older than the control subjects, so it is possible that this difference may be due to age-related factors.

The cost associated with the commercially available test of OD precludes their common use in clinical practice.

TABLE 2

AROMA and UPSIT Correlation Coefficients; ρ (p value); Total n = 68

|  | AROMA % | UPSIT % | Loss of | Age | SNOT-22 |
| --- | --- | --- | --- | --- | --- |
| AROMA % | — | .749 (<.001) | −.642 | −.557 | −.548 (<.001) |
| UPSIT % | .749 (<.001) | — | −.552 | −.460 | −.367 (.002) |
| Loss of smell* | −.642 (<.001) | −.552 (<.001) | — | .348 (.004) | .726 (<.001) |
| Age | −.557 (<.001) | −.460 (<.001) | .348 (.004) | — | .328 (.006) |
| SNOT-22 | −.548 (<.001) | −.367 (.002) | .726 | .328 (.006) | — |

*assessed on a six point ordinal scale (1, no problem-6, problem as bad as it can be).

DISCUSSION

This study reports the development and validation of AROMA, an essential oil-based test of olfactory function, against the UPSIT. The impetus for AROMA development was to create a multi-use, cost-effective, olfactory test that can be used in routine clinical testing and research. The need for such a tool is critical as smell identification and discrimination directly reflect not only the health of the sinonasal cavity, but also the cognitive state and higher cortical centers (Stockhorst U, et al. Physiol Behav. 2004 83(1):3-11; Sigurdardottir S, et al. Neuropsychology. 2016 30(1):98-108; Bastir M, et al. Nat Commun. 2011 2:588). Test-retest of AROMA was r=0.85 (p<0.001). In prospective testing of normal subjects and those with sinonasal disease of AROMA, there was a statistically significant strong correlation (r=0.75, p<0.001) between the UPSIT and AROMA.

AROMA currently costs approximately $10 per kit and is reusable for at least three months. The need for more cost-effective tools related to olfaction is underscored by a recent study by Patel et al. They investigated the use of essential oils at random concentrations for olfactory training. The results of their patients were comparable to those in studies using purchased and standardized concentrations (Patel Z M, et al. Laryngoscope Investig Otolaryngol. 2017 2(2):53-56). Interestingly, in this study that determined concentration of odorants in AROMA, several scents, such as clove and anise, in which the undiluted essential oil was overpowering and difficult for subjects to identify. For this reason, it is believed that controlled dilutions of essential oils are important for testing and, potentially, training purposes.

CONCLUSIONS

There is a need in otolaryngology and related disciplines for cost-effective, user-friendly, and adaptable olfactory testing methods. AROMA fulfills these needs and has strong correlations with the UPSIT and on test-retest. Ongoing studies are continuing to test AROMA in populations with olfactory dysfunction. Further validation and use of AROMA may ultimately allow for increased access of olfactory testing for improved disease screening and monitoring of treatment response and/or disease progression.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An olfactory diagnostic kit for screening for an olfactory dysfunction, comprising:
   a plurality of aroma inhalers, each dosed with an essential oil fragrance from a panel of from 4 to 20 diagnostic fragrances, wherein the plurality of aroma inhalers comprises and a series of different doses for each essential oil fragrance; and
   an answer key;
   wherein the answer key contains instructions that first prompts a user to use a first inhaler of a first dose of a first essential oil fragrance from the series of different doses for the first essential oil fragrance and confirm whether an aroma could be detected, wherein if an answer to the confirmation is yes, then the instructions in the answer key prompts for identification of the aroma among a list of choices, wherein if the answer is no, the answer key contains instructions for the user to try one or more subsequent inhalers of increasingly higher doses of the first essential oil fragrance from the series of different doses for the first essential oil fragrance until either the user reaches a maximum dose of the first essential oil fragrance from the series of different doses for the first essential oil fragrance or is able to provide an affirmative response to the answer to the confirmation.

2. The olfactory diagnostic kit of claim 1, wherein the answer key is displayed on a computer interface.

3. A method for diagnosing a subject for an olfactory dysfunction, comprising:
   (a) providing a panel of from 4 to 20 diagnostic fragrances;
   (b) prompting the subject to use an aroma inhaler dosed with an essential oil fragrance from the panel of diagnostic fragrances at a base dose;
   (c) prompting the subject to confirm whether an aroma could be detected, wherein if an answer to the confirmation is yes, further prompting the subject to identify the aroma from among a list of choices, wherein if the answer is no, repeating step (b) with a higher dose of the essential oil fragrance until the subject answers yes or reaches a maximum dose;
   (d) repeating steps (b) and (c) with new aroma inhalers containing the same essential oil fragrance until the subject correctly identifies the aroma at least two times in a row, or reaches a maximum number of incorrect answers; and
   (e) repeating steps (b) to (d) with each essential oil fragrance in the panel of diagnostic fragrances,
   wherein the dose at which the subject can detect the aroma and/or an inability of the subject to detect the aroma at the maximum dose diagnoses a degree of olfactory dysfunction in the subject.

4. An olfactory training kit for treating an olfactory dysfunction in a subject, comprising:
   a plurality of aroma inhalers, each dosed with an essential oil fragrance from a panel of from 4 to 20 diagnostic fragrances, wherein the plurality of aroma inhalers comprises aroma inhalers for each essential oil fragrance at different dosages; and
   an instruction key;
   wherein the panel of fragrances does not consist of rose, *eucalyptus*, lemon, and cloves; and
   wherein the instruction key identifies the respective fragrance in each aroma inhaler and prompts the subject to use each aroma inhaler for at least 5 seconds.

5. The olfactory training kit of claim 4, wherein the respective dose of the respective essential oil fragrance is personalized based on the subject's baseline olfaction.

* * * * *

UNITED STATES PATENT AND TRADEMARK OFFICE
CERTIFICATE OF CORRECTION

| | |
|---|---|
| PATENT NO. | : 12,070,319 B2 |
| APPLICATION NO. | : 17/281121 |
| DATED | : August 27, 2024 |
| INVENTOR(S) | : Jennifer Villwock and Kevin Sykes |

It is certified that error appears in the above-identified patent and that said Letters Patent is hereby corrected as shown below:

On the Title Page
Item (60), Related U.S. Application Data, Line 2, delete "62/735,585" and insert -- 62/739,585 -- therefor.

In the Claims
Column 13, Line 30, delete "and" between "comprises" and "a".

Signed and Sealed this
Fifteenth Day of October, 2024

Katherine Kelly Vidal
*Director of the United States Patent and Trademark Office*